United States Patent [19]
Austin, Jr. et al.

[11] Patent Number: 5,257,341
[45] Date of Patent: Oct. 26, 1993

[54] COMPACT IN-LINE THERMOSTATICALLY CONTROLLED ELECTRIC WATER HEATER FOR USE WITH DENTAL INSTRUMENTS

[75] Inventors: George K. Austin, Jr.; Andrew G. Schaefers, both of Newberg, Oreg.

[73] Assignee: A-Dec, Inc., Newberg, Oreg.

[21] Appl. No.: 901,557

[22] Filed: Jun. 19, 1992

[51] Int. Cl.$^5$ ............. H05B 1/02; F24H 1/14
[52] U.S. Cl. ............ 392/487; 392/488; 392/492; 433/32
[58] Field of Search ........... 433/32; 392/485–495, 392/480–484, 473–476, 479

[56] References Cited

U.S. PATENT DOCUMENTS

| | | |
|---|---|---|
| Re. 20,704 | 4/1938 | Pieper . |
| 1,351,779 | 9/1920 | Mather ................. 392/489 |
| 1,543,012 | 6/1925 | Klimis ............... 392/480 X |
| 1,595,819 | 8/1926 | Bluemlein . |
| 1,724,767 | 8/1929 | Mercer . |
| 1,807,951 | 6/1931 | Ahern ................. 392/480 |
| 2,098,732 | 11/1937 | Prather . |
| 2,390,710 | 12/1945 | Henschel ............ 392/479 X |
| 2,813,964 | 11/1957 | Cerulli ................ 392/489 |
| 3,089,941 | 5/1963 | Beu . |
| 3,638,619 | 2/1972 | Hall et al. ........... 392/487 X |
| 4,184,064 | 1/1980 | Williams . |
| 4,208,570 | 6/1980 | Rynard ............. 392/489 X |
| 4,371,777 | 1/1983 | Roller et al. . |
| 4,429,899 | 2/1981 | Davis . |
| 4,458,138 | 7/1984 | Adrian et al. . |
| 4,808,793 | 2/1989 | Hurko . |
| 4,831,236 | 5/1989 | Lentz ................. 392/481 |
| 4,871,089 | 10/1989 | Rader et al. . |
| 4,892,996 | 1/1990 | Mertes ............... 392/480 |
| 5,020,127 | 5/1991 | Eddas et al. . |

*Primary Examiner*—Anthony Bartis
*Attorney, Agent, or Firm*—Klarquist, Sparkman, Campbell, Leigh & Whinston

[57] ABSTRACT

A compact, in-line electric water heater is provided for heating water to a temperature suitable for dental operations. The heater includes a cylindrical inner tube containing an electrical heater element and a cylindrical outer tube concentrically spaced therefrom, through which water to be heated is circulated. An inlet and outlet for the water is located at one end of a chamber formed between the tubes. A control thermostat is operatively mounted on an area of the outer tube which is flattened so as to contact the inner tube and is responsive to the temperature of the outer tube. A thermal limiter is also mounted to the outer tube to function as a safety device should the control thermostat malfunction.

9 Claims, 2 Drawing Sheets

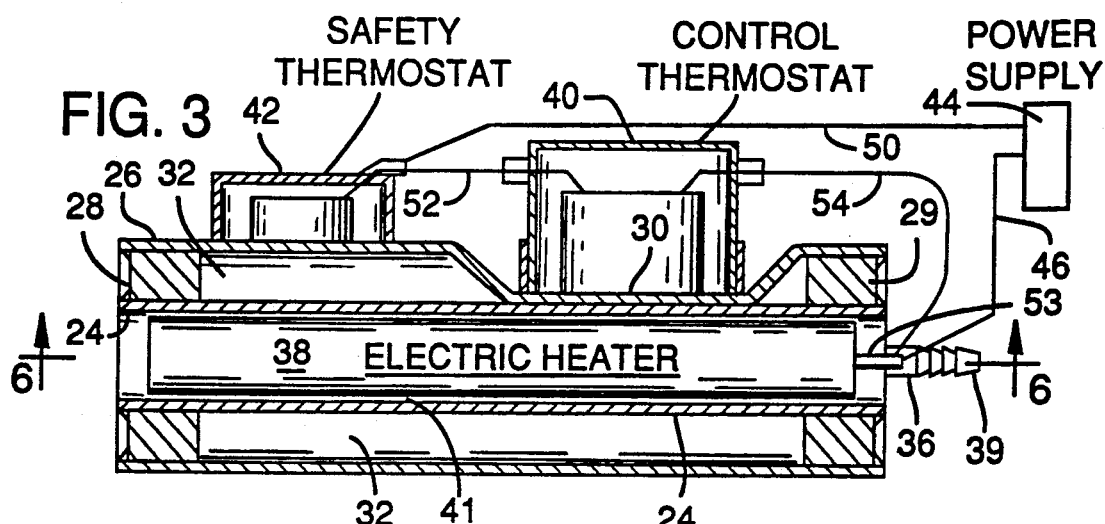
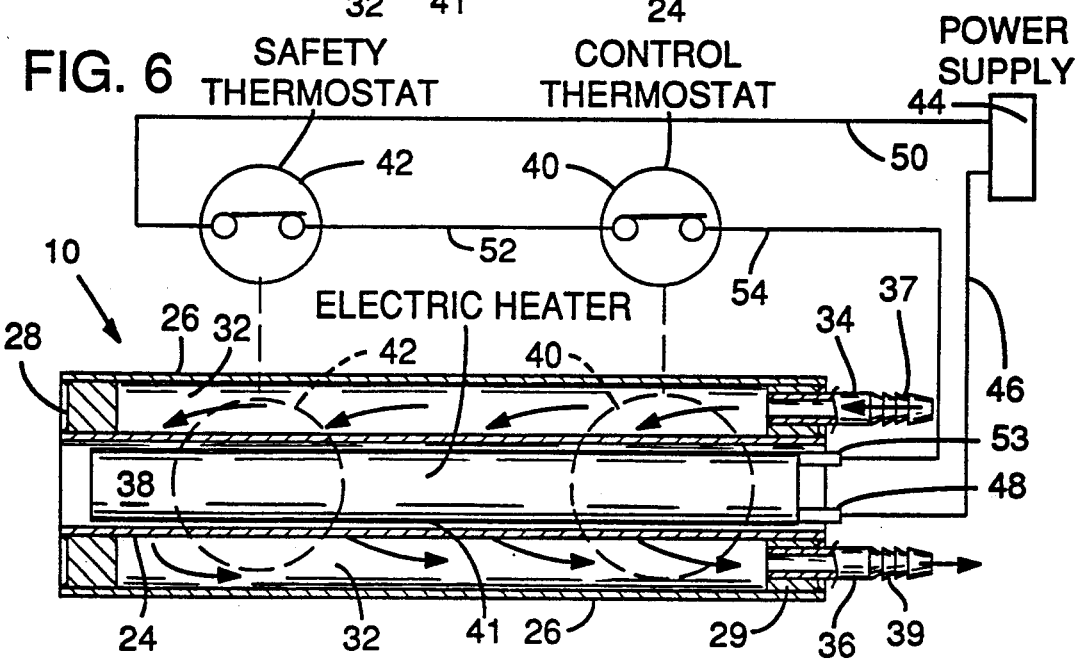
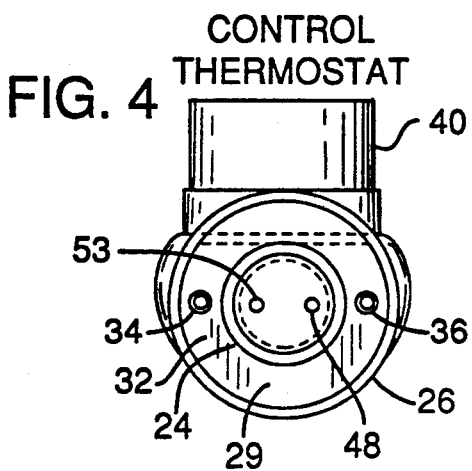
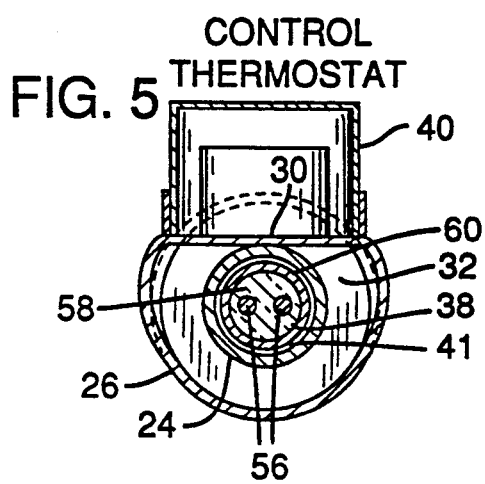

COMPACT IN-LINE THERMOSTATICALLY CONTROLLED ELECTRIC WATER HEATER FOR USE WITH DENTAL INSTRUMENTS

TECHNICAL FIELD

The present invention relates to a water heater designed for rapidly heating cold water to a temperature that is suitable for dental operations without the necessity for storing the water in a reservoir.

BACKGROUND INFORMATION

Patient's comfort is an important objective in modern dentistry. The delivery of cold fluid, such as water, into a patient's mouth during treatment can be very discomforting when the patient's teeth and gums are sensitive to sudden changes in temperature. It is a particular problem when, during the performance of certain surgical operations such as a root canal, exposed tissues in nerve endings are washed with cold water.

It is therefore desirable to preheat the water it is delivered into the patient's mouth. However, the water must not be too hot or similar undesirable effects will result. A near body temperature of the water is preferred.

Conventional water heaters for use with dental equipment are sometimes provided with a large storage container in which water is stored after it has been heated electrically. The size of the heater usually precludes mounting near the dental instruments. When water is demanded of a remotely located heater, the room temperature water in the tubing must first pass through the dental instrument before the heated water reaches the instrument. Hence, the temperature of the water at the point of use is difficult to control.

Some remote heater systems use a drip line which allows a small volume of water to constantly flow from the heater, up to the dental instrument and out through a drain. Although this system maintains warm water at the instrument, it uses a large amount of water, and a drain line must be provided.

In the prior art, rapid water heaters have been developed to heat water immediately prior to its use. Typically, these heaters are based on complicated and expensive baffle systems or thermostat designs where thermostats are submerged into the water to be heated. A thermostat based on the temperature of the water sometimes over lags the water temperature and control of the water temperature is erratic. Other water heaters include heating devices and thermostats designed into the handle of a dental syringe. One shortcoming of this design approach is that the handle is large and heavy. Many dentists supply water to the instruments from an air pressurized water bottle, rather than a municipal water supply. However, if the bottle runs dry, overheating can occur because the thermostats of many conventional heaters do not function properly in dry conditions.

SUMMARY OF THE INVENTION

It is an object of the present invention to provide a water heater that is designed to rapidly heat cold water so that the water can be passed directly from a heater to a syringe without the need for maintaining a reservoir of water.

More particularly, it is an object of the present invention to provide an efficient, compact water heater which discharges water to the syringe at a temperature that is suitable for dental operations.

It is still another object of the present invention to provide a water heater that is designed to secure a good mix of the entering cold water and the water being heated without the necessity of a baffle system.

This invention achieves these and other objectives by providing a physically small water heater that is adapted to being located in a dental control head for rapidly heating cold water so that cold water can be heated as it flows through the device and passed directly from the device to a syringe through a short length of tubing or conduit. The device includes an inner tube in which is mounted an electrical heating device and a surrounding outer tube though which flows the water to be heated. A control thermostat, responsive to a temperature of the outer tube, is mounted to a flattened area of the outer tube. The flattened area is configured so that the outer tube is in contact with the inner tube. A thermal limiter is also mounted to the outer tube to function as a safety device should the control thermostat malfunction.

BRIEF DESCRIPTION OF THE DRAWINGS

FIG. 3 is a sectional view taken along line 3—3 of FIG. 2;

FIG. 4 is an end view taken along line 4—4 of FIG. 2;

FIG. 5 is a sectional view taken along line 5—5 of FIG. 2; and

FIG. 6 is a sectional view of the device taken along line 6—6 of FIG. 3 and schematically illustrating the electrical circuits to the serially connected thermostats.

DETAILED DESCRIPTION OF A PREFERRED EMBODIMENT

Figure 1:
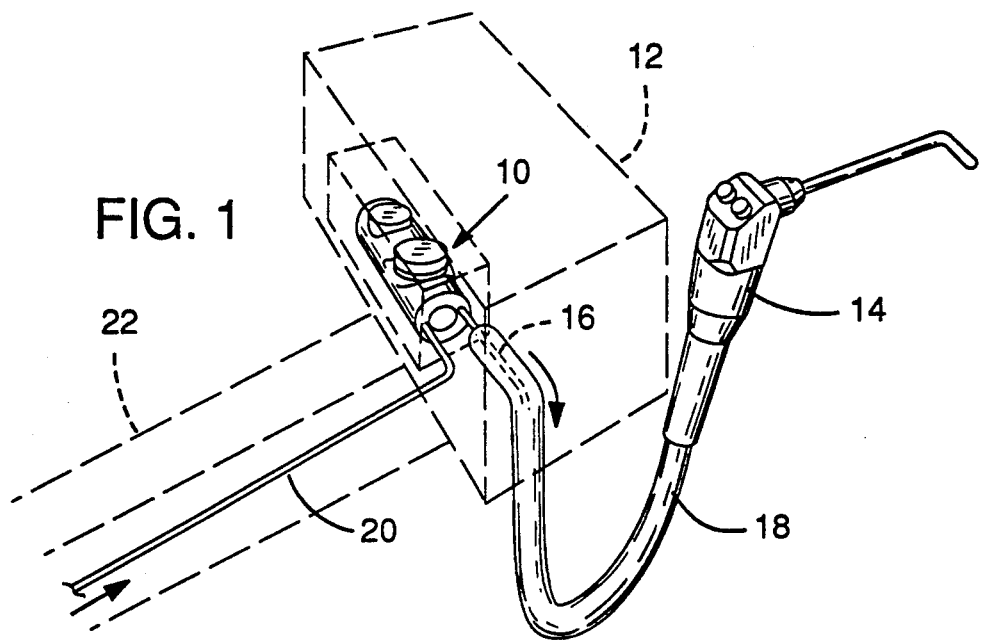
FIG. 1 is a perspective view of a water heater constructed in accordance with the invention.
Figure 2:
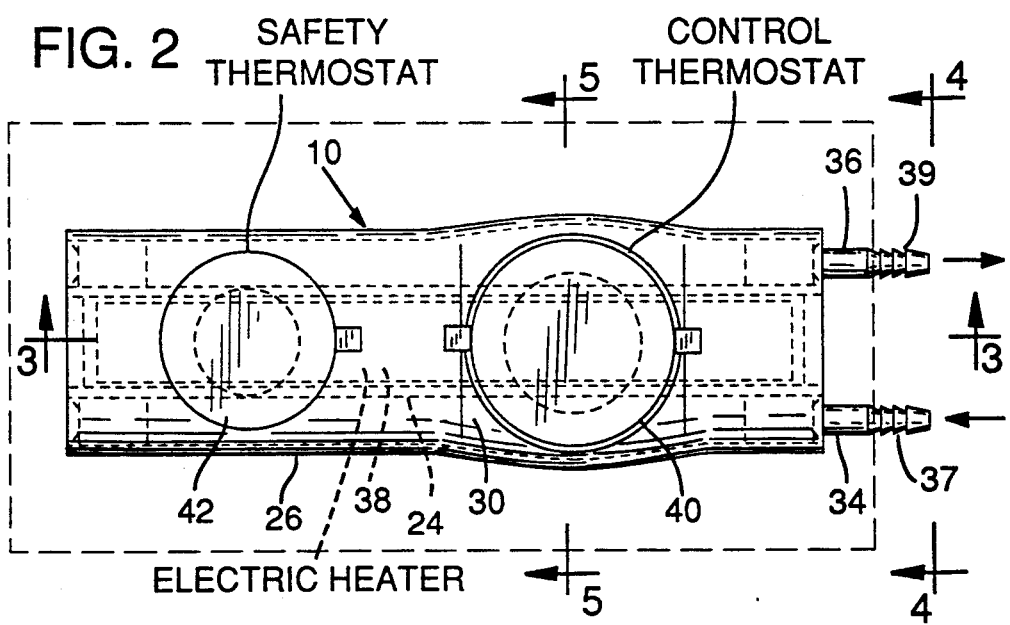
FIG. 2 is a top view of the device showing first and second thermostats mounted thereon.

Referring to the drawings, FIG. 1 illustrates a cylindrical shaped water heater 10 constructed in accordance with the present invention an positioned within a control head 12 for a dental unit. The device of the invention is particularly adapted for heating water for a dental syringe 14 to which heated water may be conducted through a short, flexible outlet conduit 16. The water heater will be described in more detail below. The outlet conduit 16 is preferable contained within an insulating outer conduit 18 for reducing any heat loss of the water flowing through the outlet conduit 16 to the syringe 14. Preferably, the control head 12 should be situated relatively close to a patient so that the outlet conduit 16 can be made as short as possible to reduce heat loss of the water flowing from the water heater 10 to the syringe 14. Water is supplied to the water heater 10 through a suitable inlet conduit 20 contained within a mounting arm 22 supporting the control head 12.

Referring to FIGS. 2-6, the water heater 10 includes a cylindrical inner tube or vessel 24 and a generally cylindrical outer tube or vessel 26 both of which are preferable made of brass or other non-corroding metal having high heat transfer capability. The outer tube 26 receives the inner tube 24 and is concentrically spaced therefrom. The opposite ends of the space between the outer tube 26 and the inner tube 24 are closed by annular end closures 28, 29. A portion of the wall of the outer tube 26 is crimped into contact with the inner tube 24, as best shown in FIG. 3, and provides a flattened peripheral surface area 30. A small amount of solder fuses the inner tube 24 to the crimped portion of the outer tube 26 for improved thermal conductivity. The significance of this contact is further explained below. The outer tube 26, except for the flattened area 30, has a greater diameter than the inner tube 24 whereby an annual chamber 32 is defined by the inner tube 24 and the outer tube 26.

The end closure 29 of the chamber 32 has a water inlet 34 and a water outlet 36 extending therethrough for conducting water into and out of the chamber 32. Both the inlet 34 and the outlet 36 are barbed as indicated at 37 and 39, respectively, for removable securement of the inlet conduit 20 and outlet conduit 16.

Referring to FIGS. 3 and 6, an electrical resistance heating device 38 of conventional construction is disposed within the inner tube 24 for heating the same thereby to heat water flowing through the chamber 32 so that water flowing out of the outlet 36 has a higher temperature than water flowing in through the inlet 34. The heating device 38 preferably comprises a resistance type heating element 56 embedded in a cylindrical ceramic body 58 which in turn is surrounded by a protective stainless steel sheath 60. A small annular gap 41 is provided between the heating device 38 and the inner tube 24. The gap 41 is filled with a silicone based heat transfer compound (not shown) to improve the transfer of heat from the heating device 38 to the inner tube 24. In a preferred embodiment of the invention, the gap 41 is about 0.005".

As shown in FIGS. 2-5, a first thermostat 40 is mounted to the outer tube 26 in the flattened area 30. The thermostat 40 is a control thermostat responsive to the temperature of the wall of the inner tube 24 through the transfer of heat to the flattened area 30 of the outer tube 26. The thermostat 40 is bonded to the flattened area 30 of the outer tube 26 by a thermally conductive bonding material, such as by a suitable epoxy adhesive. The thermostat 40 is preferably adapted to close when it senses a temperature below about 110° F. and to open at a temperature of about 130° F.

A second thermostat 42, a thermal limiter safety thermostat, is mounted to the outer tube 26 and which is normally closed at temperatures below 150° but which opens upon sensing a temperature of 150° F. The thermostat 42 is normally closed because it mainly functions as a safety device. If the thermostat 40 should malfunction and not open at temperatures above 130° F. then the thermostat 42 will open at 150° F. to prevent overheating of the water in the chamber 32. The thermostat 42 is also preferably bonded to the outer tube 26 by a heat conductive epoxy adhesive or similar material.

Referring to FIGS. 3 and 6, an electrical source 44, such as a 24-volt A.C. source, is serially connected to the heating device 38 and thermostats 40 and 42. One terminal of the electrical source 44 is connected a connector 48 of the to the heating device 38 by an electrical lead 46. The other terminal is connected by an electrical lead 50 to the thermostat 42 which is serially connected to the thermostat 40 by an electrical lead 52. The thermostat 40, in turn, is connected to the other connector 53 of the heating device 38 by an electrical lead 54.

In operation, upon water demand by the syringe 14, cold water is supplied to the water heater 10 by the inlet conduit 20 through the inlet 34 into the chamber 32. As the cold water lowers the temperature of the outer tube 26 to 110° F. the thermostat 40 closes to activate the heating device 38. Since the thermostat 40 is mounted in the flattened area 30 which is in contact with the tube 24, the thermostat is very responsive to any drop in temperature of the wall of the tube 24 beneath the desired minimum temperature. When the temperature of the water being heated, and thus the area of the outer tube 26 beneath the thermostat 40, is about 130° F., the thermostat 40 will open to open the circuit to the heating device 38 thus preventing overheating of the water. As mentioned earlier, if the thermostat 40 should malfunction and not open at about 130° F., the thermostat 42 acts as a safety mechanism and will open if the temperature of the outer tube 26 reaches about 150° F.

Eddy currents generated by the heating of water serve to secure a good mix of the entering cold water and the water being heated without the need for a baffle system. Due to the quick responsiveness of the thermostat 40, water heated to a temperature between about 110° F. and 130° F. can be supplied to the syringe 14 without having to maintain a reservoir of heated water. It is to be noted that water temperatures below 110° and above 130° F. can be supplied to syringe 14 by adjusting the thermostats 40, 42.

To reduce heat loss of the water heater 10, it can be enclosed in a casing (not shown) provided with an insulating layer between water heater 10 and the casing. Glass filled nylon and other resin matrices have been found to be suitable materials for the casing.

Having illustrated and described the principles of my invention by what is presently a preferred embodiment, it should be apparent to those persons skilled in the art that the illustrated embodiment may be modified without departing from such principles. I claim as my invention, not only the illustrated embodiment, but all such modifications, variations and equivalents thereof as come within the true spirit and scope of the following claims.

We claim:

1. A water heater for use with dental equipment, comprising:

a cylindrical inner vessel;

a cylindrical outer vessel dimensioned for receiving said inner vessel in concentrically spaced relationship thereto to define a chamber; said chamber having first and second closed ends, and means defining a fluid inlet and a fluid outlet to said chamber;

a heating device disposed in said inner vessel for heating fluid flowing through said chamber so that fluid flowing out through said outlet has a higher temperature than fluid flowing in through said inlet; and a first thermostat mounted to said outer vessel responsive to a temperature of said vessel operatively connected to said heating device for activating said heating device in response to the temperature of said outer vessel being below a first predetermined temperature, said outer vessel including a flattened area in contact with said inner vessel, said flattened area receiving said first thermostat.

2. A water heater for use with dental equipment, comprising:

an inner tube;

an outer tube of larger diameter than said inner tube and generally spaced therefrom, said outer tube receiving said inner tube to define a chamber therebetween, means closing the ends of said chamber, said outer tube including a flattened area configured so that said flattened area is in contact with said inner tube, said outer tube having first and second ends, the first end defining a fluid inlet and a fluid outlet so that fluid flowing into said chamber through said inlet flows out of said chamber through said outlet;

a heating device in said inner tube for heating fluid flowing into said chamber, and a first thermostat operatively connected to said heating device externally mounted to said outer tube in said flattened area, said thermostat being responsive to the temperature of said outer tube.

3. The water heater of claim 2 wherein said outer vessel is concentric with said inner vessel.

4. The water heater of claim 3 wherein said inner and outer vessels are cylindrical.

5. The water heater of claim 2 wherein said inlet is proximate to said outlet.

6. The water heater of claim 2 wherein said tubes are made of a heat conductive material.

7. The water heater of claim 2 wherein said heat conductive material is brass.

8. The water heater of claim 2 wherein said water heater includes a cut-off thermostat operatively connected to said heating device and said first thermostat and mounted on said outer tube so as to be responsive to the temperature of said outer tube.

9. A water heater for use with dental equipment comprising:

a cylindrical inner vessel;

a generally cylindrical outer vessel receiving the inner vessel, said inner and outer vessels being concentrically spaced with the space therebetween closed at its ends to define an annular chamber, the outer vessel having a flattened peripheral area configured so that said flattened area is in contact with said inner vessel whereby the said flattened area is substantially at the temperature of the inner vessel, said outer vessel except for said flattened area being of greater diameter than said inner vessel, one end of said chamber having a fluid inlet and a fluid outlet therein for conducting fluid into and out of said chamber;

an electrical resistance heating device disposed within the inner vessel for heating the same thereby to heat fluid flowing through said chamber so that fluid flowing through the fluid outlet has a higher temperature than fluid flowing in through the fluid inlet;

a first thermostat mounted to the outer vessel in said flattened area thereof and responsive to the temperature of the outer vessel for activating the heating device when the temperature of the outer vessel is below about 110° F. and deactivating said heating device when the temperature is about 130° F.;

a second thermostat mounted to the outer vessel responsive to the temperature of the outer vessel for deactivating the heating device when the temperature of the outer vessel reaches about 150° F.; and circuit means for serially connecting said heating device and said thermostats to a source of electrical energy.

* * * * *

UNITED STATES PATENT AND TRADEMARK OFFICE
CERTIFICATE OF CORRECTION

PATENT NO. : 5,257,341
DATED : October 26, 1993
INVENTOR(S) : George K. Austin

It is certified that error appears in the above-indentified patent and that said Letters Patent is hereby corrected as shown below: Title page, item [57] col. 2,

In the Abstract:

Lines 4, "heater" should be --heating--;

Column 1, line 21, "water_____it is" should be --water before it is--;

Column 2, line 15, "though which" should be --through which--;

Column 2, line 43, "invention an" should be --invention and--;

Column 2, line 49, "preferable" should be --preferably--;

Column 2, line 62, "preferable" should be --preferably--;

Column 3, line 57, "connected a" should be --connected to a--;

UNITED STATES PATENT AND TRADEMARK OFFICE
CERTIFICATE OF CORRECTION

PATENT NO. : 5,257,341
DATED : October 1, 1993
INVENTOR(S) : George K. Austin

It is certified that error appears in the above-indentified patent and that said Letters Patent is hereby corrected as shown below:

Column 3, line 58, "of the to the heating" should be --of the heating

Signed and Sealed this

Third Day of January, 1995

Attest:

Attesting Officer

BRUCE LEHMAN

Commissioner of Patents and Trademarks